United States Patent
Haberland et al.

(10) Patent No.: US 7,153,319 B1
(45) Date of Patent: Dec. 26, 2006

(54) TROCAR SYSTEM HAVING SHIELDED TROCAR

(75) Inventors: Gary Haberland, Orlando, FL (US); Sam R. Marchand, Dunedin, FL (US); Steve Nilson, Ocala, FL (US); Robert Sean Hagen, Winter Park, FL (US); Bennie W. Gladdish, Jr., Odessa, FL (US)

(73) Assignee: Genico, Inc., Winter Park, FL (US)

( * ) Notice: Subject to any disclaimer, the term of this patent is extended or adjusted under 35 U.S.C. 154(b) by 0 days.

(21) Appl. No.: 09/580,721

(22) Filed: May 30, 2000
(Under 37 CFR 1.47)

Related U.S. Application Data

(63) Continuation-in-part of application No. 29/117,520, filed on Jan. 26, 2000, now Pat. No. Des. 449,887.

(51) Int. Cl.
*A61B 17/34* (2006.01)
(52) U.S. Cl. ...................................... 606/185
(58) Field of Classification Search ............... 606/185; 604/164.01, 167.01, 167.02, 167.03, 167.04, 604/167.06
See application file for complete search history.

(56) References Cited

U.S. PATENT DOCUMENTS

| | | | |
|---|---|---|---|
| 3,861,416 A | 1/1975 | Wichterle | 137/525.3 |
| 3,994,287 A | 11/1976 | Turpe et al. | 128/6 |
| 4,143,853 A | 3/1979 | Abramson | 251/149 |
| 4,177,814 A | 12/1979 | Knepshield et al. | 128/348 |
| 4,222,126 A | 9/1980 | Boretos et al. | 3/1.5 |
| 4,233,982 A | 11/1980 | Bauer et al. | 128/347 |
| 4,364,127 A | 12/1982 | Pierce et al. | 3/1.5 |
| 4,375,864 A | 3/1983 | Savage | 222/81 |
| 4,424,833 A | 1/1984 | Spector et al. | 137/849 |
| 4,475,548 A | 10/1984 | Muto | 128/207.14 |
| 4,492,253 A | 1/1985 | Raftis | 137/849 |
| 4,535,773 A | 8/1985 | Yoon | 604/51 |
| 4,535,819 A | 8/1985 | Atkinson et al. | 137/846 |
| 4,566,493 A | 1/1986 | Edwards et al. | 137/846 |
| 4,601,710 A | 7/1986 | Moll | 604/165 |
| 4,654,030 A | 3/1987 | Moll et al. | 604/165 |

(Continued)

FOREIGN PATENT DOCUMENTS

EP    0 617 924 A2    9/1994    ............... 17/34

(Continued)

*Primary Examiner*—Michael Thaler

(57) ABSTRACT

A trocar system is provided which preferably includes a cannula having an elongate cannula body. The cannula body includes medial and distal portions thereof having a first diameter and a proximal portion thereof connected to the medial portion and having a second diameter. The second diameter is preferably larger or greater than the first diameter. A trocar having an elongate trocar body also extends through the cannula. The elongate trocar body has a sharpened distal end portion, a medial portion thereof having a first diameter, and a proximal portion having a second diameter. The second diameter is preferably larger or greater than the first diameter. The trocar also has a handle connected to a proximal end portion of the trocar body for gripping of and handling of the trocar by a hand of a user and a shield slidably mounted to the medial portion of the trocar body and biased in an extended position so that a distal end of the shield coveringly protects the sharpened distal end of the trocar body until pressure is applied thereagainst so that the shield slidably moves toward the proximal portion of the trocar body in a retracted position. The shield has a third diameter which is preferably at least equal to or less than the second diameter.

10 Claims, 6 Drawing Sheets

U.S. PATENT DOCUMENTS

| | | | |
|---|---|---|---|
| 4,673,393 A | 6/1987 | Suzuki et al. | 604/167 |
| 4,705,709 A | 11/1987 | Vailancourt | 428/36 |
| 4,765,588 A | 8/1988 | Atkinson | 251/149.1 |
| 4,798,584 A | 1/1989 | Hancock et al. | 604/93 |
| 4,798,593 A | 1/1989 | Iwatschenko | 604/164 |
| 4,809,679 A | 3/1989 | Shimonaka et al. | 128/4 |
| 4,876,126 A | 10/1989 | Takemura et al. | 428/35.7 |
| 4,902,280 A | 2/1990 | Lander | 604/165 |
| 4,906,237 A | 3/1990 | Johansson et al. | 604/265 |
| 4,931,042 A | 6/1990 | Holmes et al. | 604/164 |
| 4,943,280 A | 7/1990 | Lander | 604/169 |
| 4,977,901 A | 12/1990 | Ofstead | 128/772 |
| 4,990,357 A | 2/1991 | Karakelle et al. | 427/2 |
| 5,009,391 A | 4/1991 | Steigerwald | 251/167 |
| 5,010,925 A | 4/1991 | Atkinson et al. | 137/847 |
| 5,030,206 A | 7/1991 | Lander | 604/164 |
| 5,041,095 A | 8/1991 | Littrell | 604/167 |
| 5,053,016 A | 10/1991 | Lander | 604/169 |
| 5,066,288 A | 11/1991 | Deniega et al. | 604/274 |
| 5,104,382 A | 4/1992 | Brinkerhoff et al. | 604/165 |
| 5,104,383 A | 4/1992 | Shichman | 604/167 |
| 5,112,321 A | 5/1992 | Hiltebrandt | 604/264 |
| 5,122,122 A | 6/1992 | Allgood | 604/174 |
| 5,127,909 A | 7/1992 | Shichman | 604/165 |
| 5,129,885 A | 7/1992 | Green et al. | 604/164 |
| 5,141,498 A | 8/1992 | Christian | 604/167 |
| 5,147,316 A | 9/1992 | Castillenti | 604/164 |
| 5,152,754 A | 10/1992 | Plyley et al. | 604/164 |
| 5,209,737 A | 5/1993 | Ritchart et al. | 604/167 |
| 5,217,441 A | 6/1993 | Shichman | 604/283 |
| 5,224,951 A | 7/1993 | Freitas | 606/172 |
| 5,226,890 A | 7/1993 | Ianniruberto et al. | 604/164 |
| 5,226,891 A | 7/1993 | Bushatz et al. | 604/165 |
| 5,248,298 A | 9/1993 | Bedi et al. | 604/51 |
| 5,267,965 A | 12/1993 | Deniega | 604/164 |
| 5,273,545 A | 12/1993 | Hunt et al. | 604/167 |
| 5,292,310 A | 3/1994 | Yoon | 604/158 |
| 5,300,036 A | 4/1994 | Mueller et al. | 604/167 |
| 5,308,336 A | 5/1994 | Hart et al. | 604/167 |
| 5,309,896 A | 5/1994 | Moll et al. | 128/20 |
| 5,334,166 A | 8/1994 | Palestrant | 604/265 |
| 5,338,305 A | 8/1994 | Plyley et al. | 604/164 |
| 5,342,315 A | 8/1994 | Rowe et al. | |
| 5,344,420 A | 9/1994 | Hilal et al. | 606/28 |
| 5,350,364 A | 9/1994 | Stephens et al. | |
| 5,360,417 A | 11/1994 | Gravener et al. | 604/278 |
| 5,364,408 A | 11/1994 | Gordon | 606/144 |
| 5,366,478 A | 11/1994 | Brinkerhoff et al. | |
| 5,368,607 A | 11/1994 | Freitas | 606/185 |
| D354,565 S | 1/1995 | Medema | D24/146 |
| 5,385,552 A | 1/1995 | Haber et al. | 604/167 |
| 5,385,553 A | 1/1995 | Hart et al. | 604/167 |
| 5,389,081 A | 2/1995 | Castro | 604/167 |
| 5,391,154 A | 2/1995 | Young | 604/167 |
| 5,397,335 A | 3/1995 | Gresl et al. | |
| 5,407,433 A | 4/1995 | Loomas | 604/167 |
| 5,411,483 A | 5/1995 | Loomas et al. | 604/167 |
| 5,431,666 A | 7/1995 | Sauer et al. | 606/139 |
| 5,443,452 A | 8/1995 | Hart et al. | 604/167 |
| 5,445,617 A | 8/1995 | Yoon | 604/165 |
| 5,456,284 A | 10/1995 | Ryan et al. | 137/522 |
| D364,924 S | 12/1995 | Medema | D24/146 |
| 5,476,475 A | 12/1995 | Gadberry | 606/185 |
| 5,492,304 A | 2/1996 | Smith et al. | 251/149 |
| 5,496,280 A | 3/1996 | Vandenbroek et al. | 604/167 |
| 5,496,289 A | 3/1996 | Wenstrom, Jr. | 604/264 |
| 5,497,433 A | 3/1996 | Itoh et al. | |
| 5,507,755 A | 4/1996 | Gresl et al. | 606/139 |
| 5,527,321 A | 6/1996 | Hinchliffe | 606/144 |
| 5,538,509 A | 7/1996 | Dunlap et al. | 604/264 |
| 5,542,931 A | 8/1996 | Gravener et al. | 604/167 |
| 5,545,150 A | 8/1996 | Danks et al. | 604/265 |
| 5,569,206 A | 10/1996 | Gorman, Jr. et al. | 604/167 |
| 5,575,800 A | 11/1996 | Gordon | 606/144 |
| 5,578,044 A | 11/1996 | Gordon et al. | 606/144 |
| 5,584,850 A | 12/1996 | Hart et al. | 606/185 |
| 5,603,702 A | 2/1997 | Smith et al. | 604/256 |
| 5,618,290 A | 4/1997 | Toy et al. | 606/139 |
| 5,618,297 A | 4/1997 | Hart et al. | 606/185 |
| 5,628,732 A | 5/1997 | Antoon, Jr. et al. | |
| 5,634,908 A | 6/1997 | Loomas | |
| 5,637,108 A | 6/1997 | Vidal et al. | 606/1 |
| 5,657,963 A | 8/1997 | Hinchliffe et al. | 251/149.1 |
| 5,662,615 A | 9/1997 | Blake, III | |
| 5,674,237 A | 10/1997 | Ott | 606/185 |
| 5,676,683 A | 10/1997 | Yoon | 606/185 |
| 5,688,286 A | 11/1997 | Yoon | 606/185 |
| 5,690,663 A | 11/1997 | Stephens | 606/185 |
| 5,709,664 A | 1/1998 | Vandenbroek et al. | 604/167 |
| 5,709,671 A | 1/1998 | Stephens et al. | 604/264 |
| 5,713,910 A | 2/1998 | Gordon et al. | 606/144 |
| 5,720,730 A | 2/1998 | Blake, III | |
| 5,720,759 A | 2/1998 | Green et al. | 606/167 |
| 5,722,958 A | 3/1998 | Gravener et al. | 604/169 |
| 5,727,770 A | 3/1998 | Dennis | |
| 5,730,755 A | 3/1998 | Yoon | 606/185 |
| 5,741,279 A | 4/1998 | Gordon et al. | 606/144 |
| 5,752,938 A | 5/1998 | Flatland et al. | |
| 5,772,672 A | 6/1998 | Toy et al. | 606/139 |
| 5,776,112 A | 7/1998 | Stephens et al. | 604/264 |
| 5,782,812 A | 7/1998 | Hart et al. | 604/167 |
| 5,792,112 A | 8/1998 | Hart et al. | 604/167 |
| 5,792,113 A | 8/1998 | Kramer et al. | |
| 5,803,919 A | 9/1998 | Hart et al. | 604/167 |
| 5,807,338 A | 9/1998 | Smith et al. | 604/164 |
| 5,810,866 A | 9/1998 | Yoon | 606/185 |
| 5,824,009 A | 10/1998 | Fukuda et al. | 606/144 |
| 5,827,228 A | 10/1998 | Rowe | |
| 5,865,807 A | 2/1999 | Blake, III | |
| 5,871,488 A | 2/1999 | Tovey et al. | 606/139 |
| 5,895,377 A | 4/1999 | Smith et al. | 604/256 |
| 5,935,107 A | 8/1999 | Taylor et al. | 604/164 |
| 5,980,493 A | 11/1999 | Smith et al. | 604/164 |
| 5,989,224 A | 11/1999 | Exline et al. | |
| 6,217,555 B1 | 4/2001 | Hart et al. | |
| 6,228,061 B1 | 5/2001 | Flatland et al. | |
| 6,258,065 B1 | 7/2001 | Dennis et al. | |
| 6,482,181 B1 | 11/2002 | Racenet et al. | |
| 6,551,282 B1 | 4/2003 | Exline et al. | |
| 6,595,946 B1 | 7/2003 | Pasqualucci et al. | |
| 6,612,196 B1 | 9/2003 | Petzold | |
| 6,702,787 B1 | 3/2004 | Racenet al. | |

FOREIGN PATENT DOCUMENTS

| | | | |
|---|---|---|---|
| EP | 0617924 A2 | 10/1994 | |

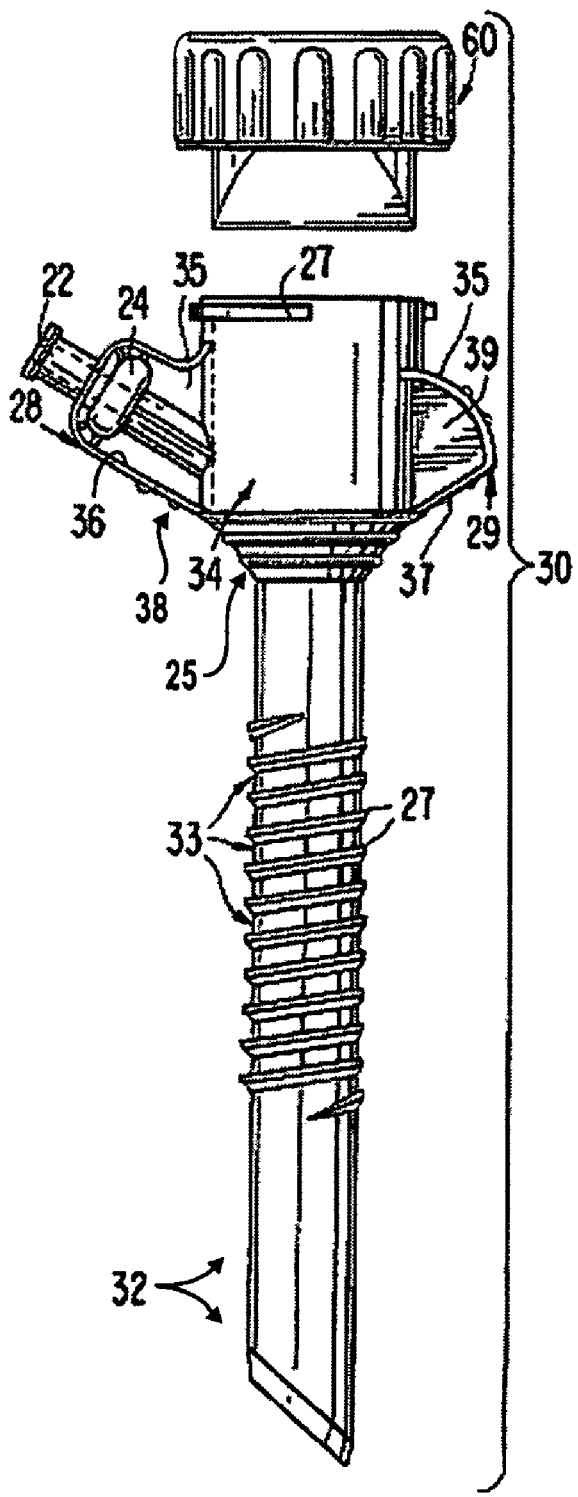
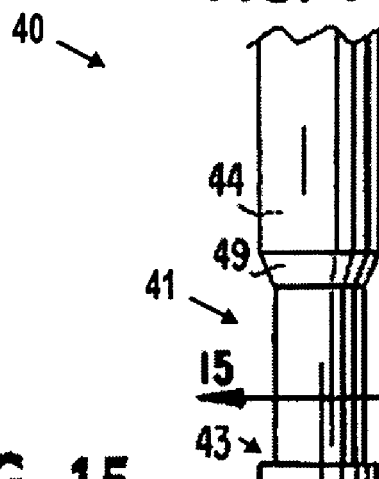
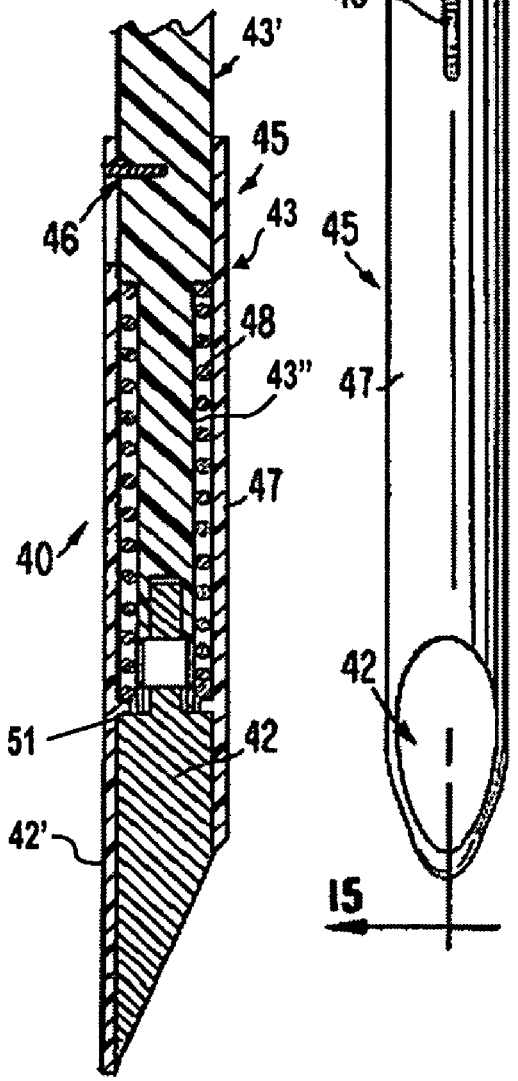

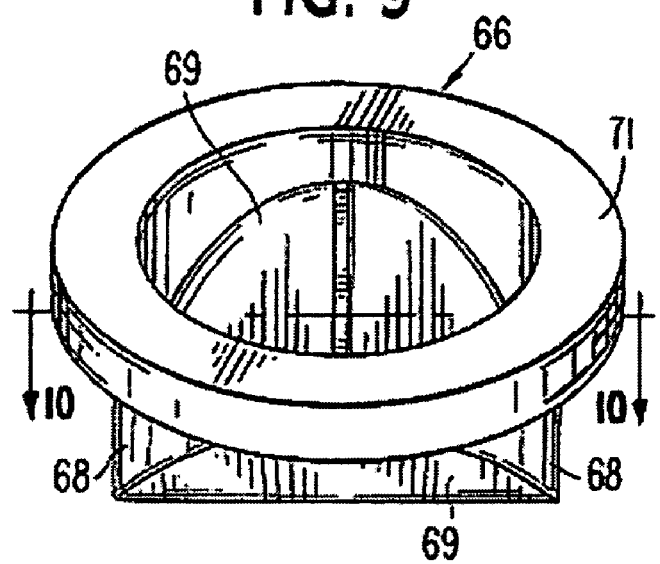
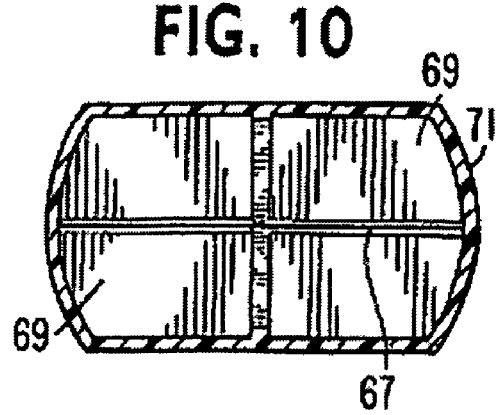
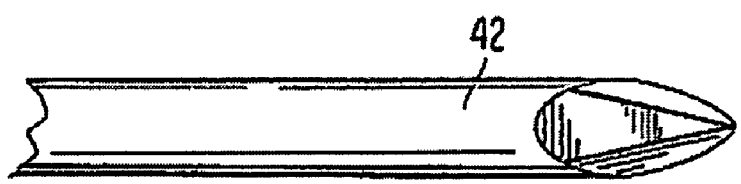
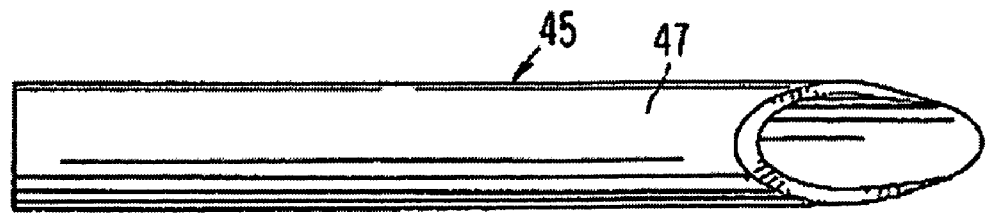

TROCAR SYSTEM HAVING SHIELDED TROCAR

RELATED APPLICATIONS

This application is a continuation-in-part of U.S. Design Patent Application No. 29/117,520 filed on Jan. 26, 2000, now U.S. Pat. No. Des. 449,887, the entire disclosure of which is hereby incorporated herein by reference in its entirety.

FIELD OF THE INVENTION

The present invention relates to the field of medical devices and, more particularly, to trocar systems and methods.

BACKGROUND OF THE INVENTION

Trocar systems have been developed over the years for various endoscopic applications in the field of medicine. These trocar systems conventionally include a cannula through which a trocar or obturator or other endoscopic related tool extends. The trocar can be shielded or unshielded. Examples of shielded trocars can be seen in U.S. Pat. No. 4,654,030 by Moll et al. titled "Trocar," U.S. Pat. No. 4,931,042 by Holmes et al. titled "Trocar Assembly With Improved Latch," U.S. Pat. No. 4,902,280 by Lander titled "Trocar," and U.S. Pat. No. 5,030,206 by Lander titled "Trocar." Other shielded trocars which are more cost effective to manufacture, less bulky to handle and ship, and yet produce reliable performance, however, are still needed.

It is also known to use one or more valves positioned within or connected to a proximal end of the cannula of a trocar system. Examples of such trocar systems having one or more valves in the cannula thereof can be seen in U.S. Pat. No. 5,226,891 by Bushatz et al. titled "Seal Protection Apparatus," U.S. Pat. No. 5,308,336 by Hart et al. titled "Seal Protection Mechanism," U.S. Pat. No. 5,385,553 by Hart et al. titled "Trocar With Floating Septum Seal," U.S. Pat. No. 5,782,812 by Hart et al. titled "Seal Assembly For Access Device," U.S. Pat. No. 5,443,452 by Hart et al. titled "Seal Assembly For Access Device," and U.S. Pat. No. 5,209,737 by Ritchart et al. titled "Lever Actuated Septum Seal."

These devices, however, often have complex mechanical valves which can be difficult and expensive to manufacture. Accordingly, after use in surgical procedures, e.g., endoscopic, the cannulas having the valves therein are often thrown away, especially if they are not sterilizable. Therefore, this expensive cost is often past on to insurance providers and patients whom upon whom they are used.

Others of these valves for cannulas of trocar systems do not have complex mechanical valves, but can still be expensive or more difficult to manufacture. As costs often rise in the health care industry, insurance, consumers, and governmental agencies often strive to drive prices for medical devices down. Also, these other valves are often not flexible for various uses by physicians or medical personnel during surgical procedures and often can be damaged. Accordingly, there is also still a need for alternative cannula and valve configurations for trocar systems, a need less expensive trocar systems, a need for more flexible trocar systems which enhance handling thereof by medical personnel users, i.e., physicians, and trocar systems which are still effective for various endoscopic surgical procedures.

SUMMARY OF THE INVENTION

With the foregoing in mind, the present invention advantageously provides a trocar system having relatively low costs associated with the manufacturing of components of the system, e.g., cannula, trocar, valves, and thereby reduces the cost associated with the trocar system. The present invention also advantageously provides a trocar system which enhances handling by physicians or medical personnel during surgical procedures. The present invention additionally advantageously provides a more flexible trocar system which is effective during various endoscopic surgical procedures. The present invention still also advantageously provides a cannula and a trocar which each are more ergonomic and easy to use, The present invention further advantageously provides enhanced methods of using and handling a trocar system during surgical procedures.

More particularly, the present invention advantageously provides a trocar system which includes a cannula having an elongate cannula body. The cannula body includes medial and distal portions thereof having a first diameter and a proximal portion thereof connected to the medial portion and having a second diameter. The second diameter is preferably larger or greater than the first diameter. A trocar having an elongate trocar body also extends through the cannula. The elongate trocar body has a sharpened distal end portion, a medial portion thereof having a first diameter, and a proximal portion having a second diameter. The second diameter is preferably larger or greater than the first diameter. The trocar also has a handle connected to a proximal end portion of the trocar body for gripping of and handling of the trocar by a hand of a user and a shield slidably mounted to the medial portion of the trocar body and biased in an extended position so that a distal end of the shield coveringly protects the sharpened distal end of the trocar body until pressure is applied thereagainst so that the shield slidably moves toward the proximal portion of the trocar body in a retracted position. The shield has a third diameter which is preferably at least equal to or less than the second diameter.

BRIEF DESCRIPTION OF THE DRAWINGS

Some of the features, advantages, and benefits of the present invention having been stated, others will become apparent as the description proceeds when taken in conjunction with the accompanying drawings in which:

FIG. 2 is a side elevational view of a trocar system according to the present invention;

FIG. 7 is a top plan view of an obturator removed from the shield of a shielded obturator of a trocar system according to the present invention;

FIG. 8 is a top plan view of a shield of a shielded obturator of a trocar system according to the present invention;

FIG. 9 is a perspective view of a secondary valve of a trocar system according to the present invention;

FIG. 10 is sectional view of a secondary valve of a trocar system taken along line 10—10 of FIG. 9 according to the present invention;

FIG. 14 is an enlarged fragmentary side plan view of a shielded trocar of a trocar cording to the present invention; and FIG. 15 is a sectional view of a shielded trocar of a trocar system taken along line FIG. 14 according to the present invention.

DETAILED DESCRIPTION OF PREFERRED EMBODIMENTS

The present invention will now be described more fully hereinafter with reference to the accompanying drawings which illustrate preferred embodiments of the invention. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, the prime notation, if used, indicates similar elements in alternative embodiments.

Figure 1:
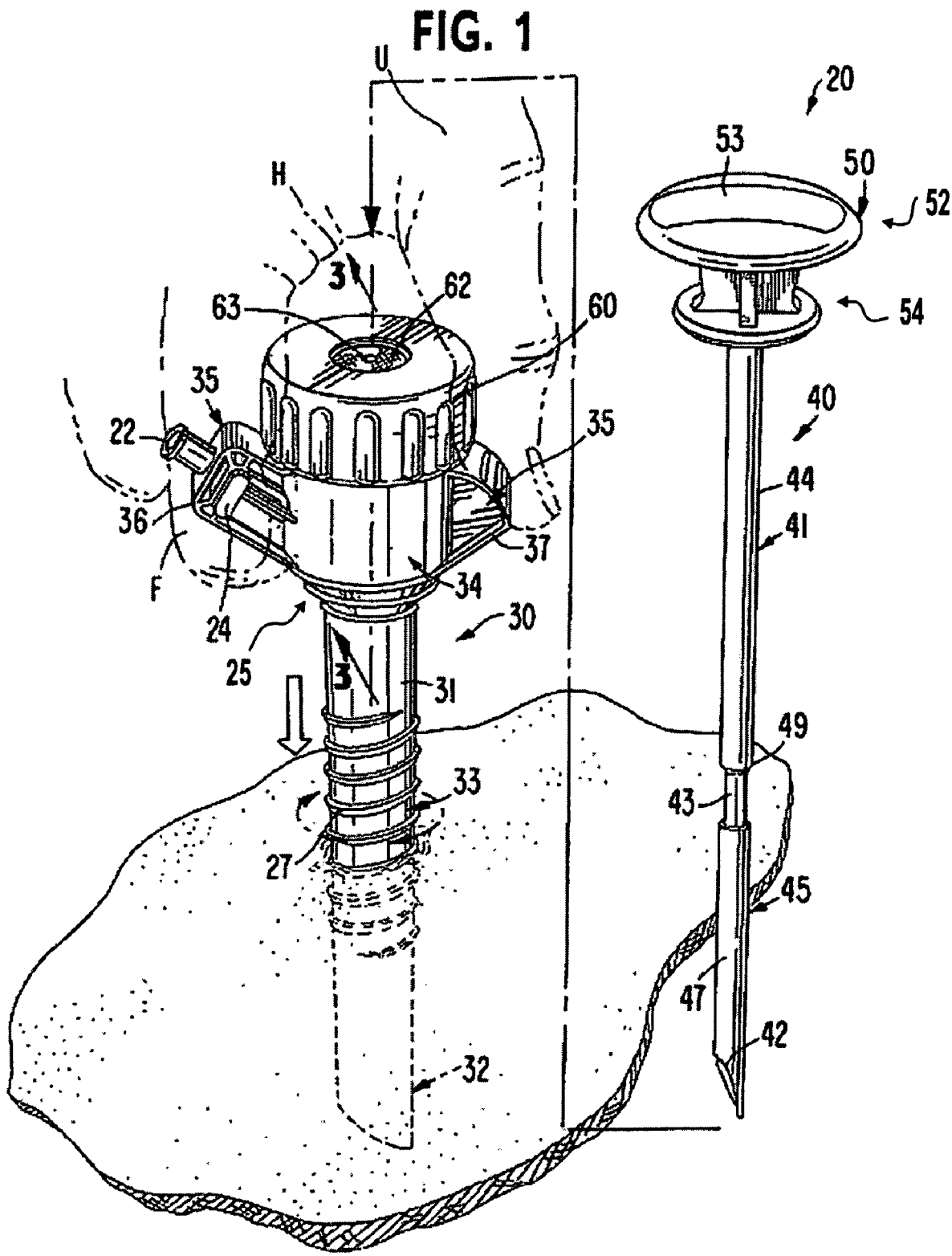
FIG. 1 is a perspective environmental view of a trocar system positioned within a layer of epidermis of a patient according to the present invention.

FIG. 1 illustrates a trocar system 20 which preferably includes a cannula 30 having an elongate cannula body 31. The cannula body 31 includes distal 32 and medial 33 portions thereof having a first diameter and a proximal portion 34 thereof connected to the medial portion 33 and having a second diameter. The second diameter is preferably larger than or greater than the first diameter as illustrated. The trocar system 20 also has finger gripping means 35 connected to and extending outwardly from the proximal portion 34 of the cannula body 31 for gripping the cannula 30 with the fingers F of a hand H of a user U and a trocar 40 having an elongate trocar body 41 for extending through the cannula 30. The trocar 40 also has a handle 50 including a proximal handle end portion 52 and a distal handle end portion 54 having a diameter smaller than the proximal handle end portion 52 and connected to the trocar body 41 for gripping of and handling of the trocar 40 by a hand H of a user U.

Figure 3:
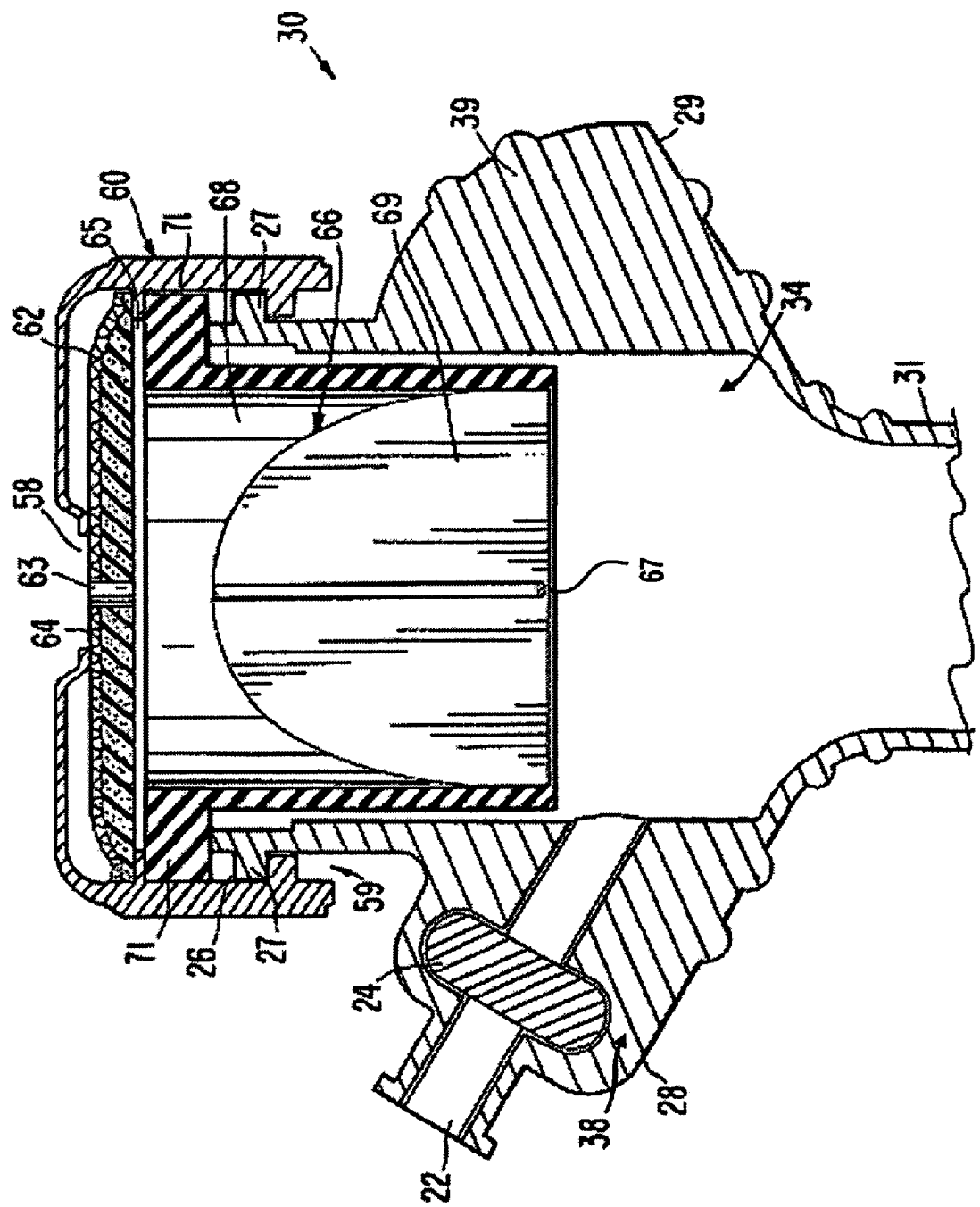
FIG. 3 is a fragmentary sectional view of a trocar system having primary and secondary valves taken along line 3—3 of FIG. 1 according to the present invention.

As perhaps best shown in FIGS. 1–3, the finger gripping means 35 of the trocar system 20, for example, can be provided by a pair of finger grips 36, 37 connected to outer surfaces of the proximal portion of the cannula body. Each of the pair of finger grips includes a finger support web 38, 39 to thereby define a pair of finger support webs. Each of the pair of finger support webs 38, 39 is connected at a position substantially 180 degrees from the other of the pair as illustrated. The medial portion 33 of the cannula body 31 connects to the proximal portion 34 of the cannula body at an area defining a proximal transition region 25. Each of the pair of support webs 38, 39 has a distal peripheral surface 28, 29 which extends outwardly from the proximal portion 34 of the cannula body 31 and extends proximally from a plane substantially perpendicular to the transition region 25 of the cannula body 31.

Also, each of the tactile finger support webs 38, 39 preferably has a roughened or ridged outer peripheral surface for reducing finger slippage when positioned on the finger support webs 38, 39 (see FIG. 2). Each of the pair of finger support webs 38, 39 are preferably formed integrally with the cannula body 31 as a single piece. At least one of the pair of finger support webs 38 includes an auxiliary fluid port 22 extending through a medial portion of the finger support web 38 to allow fluid, e.g., gas or liquid, to flow therethrough. A flow control valve 24, e.g., a stop flow or on/off flow valve which slidably extends across the port 22, is associated with the auxiliary fluid port 22 of the at least one 38 of the pair of finger support webs 38, 39 for controlling fluid flow, such as carbon dioxide, through the auxiliary fluid port 22 to the inner tubular portions of the cannula as illustrated.

Additionally, the medial portion 33 of the cannula body 31 includes a plurality of rib members 27 formed integrally with and extending outwardly from the outer surface of the cannula body 31. As understood by those skilled in the art, the rib members form fascia threads, but the medial portion can be smooth as well. The distal end portion 32 has peripheral cannula opening portions which are beveled and angle proximally from a first plane extending substantially perpendicular to a distal end of the distal portion of the cannula body 31 and extend along a second plane transverse to the first plane. The distal end portion, in essence, has distal bevel sheds forming a pre-peritoneal tent. The trocar body 41 of the trocar 40 has a sharpened distal end portion 42 and a shield 47 at least partially covering the distal end 42.

According to additional aspects of the present invention, a cannula body end housing 60 is readily detachably connected to the proximal portion 34 of the cannula body 31 for housing at least one valve therein. First and second trocar valves 62, 66 are either positioned substantially within or have portions positioned within the cannula body end housing 60 as illustrated, and each has an opening 63, 67 in a medial portion thereof. The first valve 62 is positioned proximal of the second valve 66 and is preferably positioned entirely within the housing 60 as shown. The trocar 40 has an elongate trocar body 41 which also extends through the cannula body end housing 60, the respective openings 63, 67 of the first and second trocar valves, and the cannula body 31.

Figure 4:
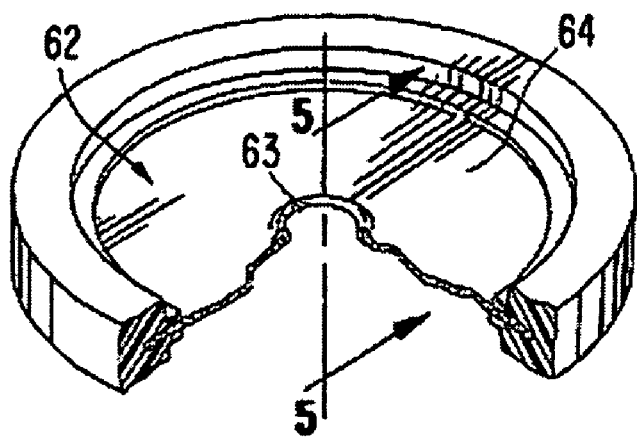
FIG. 4 is a fragmentary perspective view of a primary valve of a trocar system according to the present invention.
Figure 5:
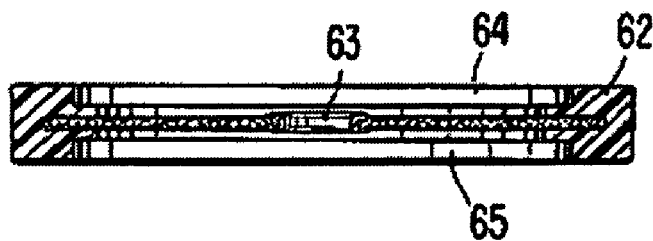
FIG. 5 is a sectional view of a primary valve of a trocar system taken along line 5—5 of FIG. 4 according to the present invention.
Figure 6:
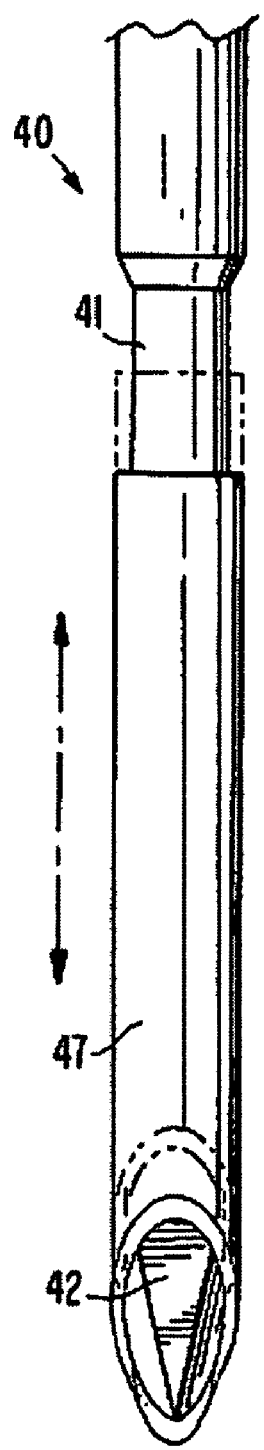
FIG. 6 is a fragmentary top plan view of a shielded obturator of a trocar system according to the present invention.
Figure 11:
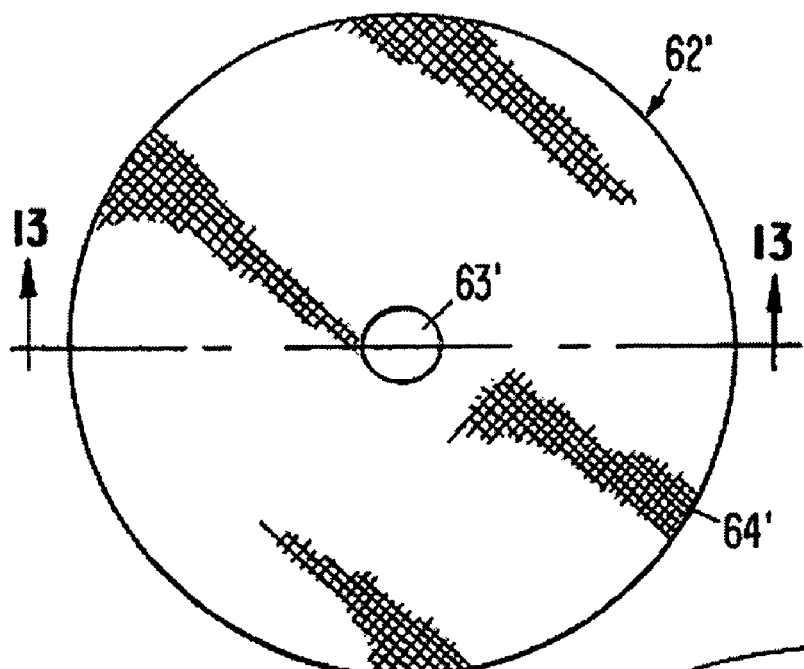
FIG. 11 is a top plan view of another embodiment of a primary valve of a trocar system according to the present invention.
Figure 12:
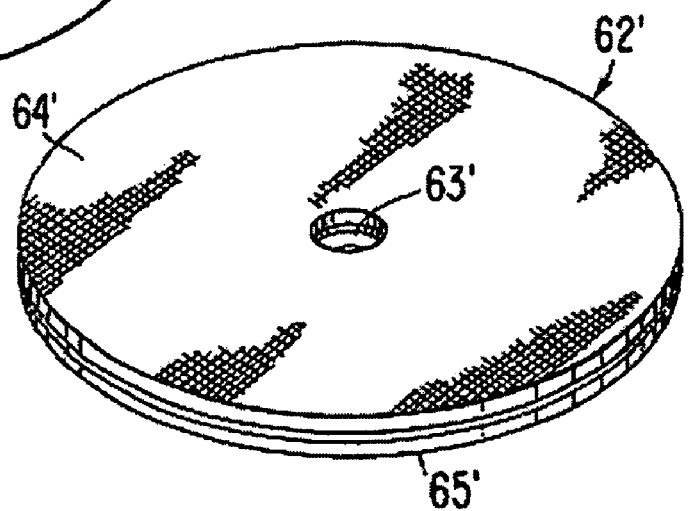
FIG. 12 is a perspective view of another embodiment of a primary valve of a trocar cording to the present invention.
Figure 13:
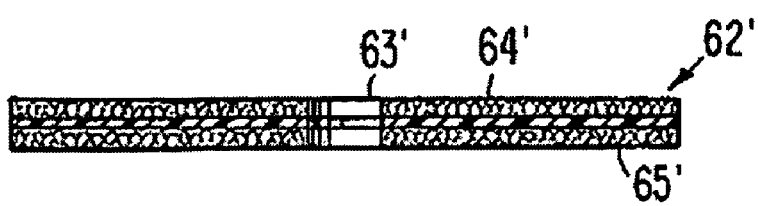
FIG. 13 is a sectional view of another embodiment of a primary valve of a trocar ken along line 13—13 of FIG. 11 according to the present invention.

The first or primary valve 62 is preferably formed of an elastomeric material which slidably deforms around the body of the trocar 40 when positioned therein to seal outer peripheries of the trocar body 41 abuttingly contacting inner peripheries of the opening 63 of the first valve 62. The first valve 62 has a substantially planar proximal surface 64 and a substantially planar distal surface 65. In a first embodiment of the first or primary valve, the elastomeric material preferably includes a fibrous material being impregnated with a silicon material to enhance the strength of the valve 62 and to enhance sliding and sealing of the body 41 of the trocar 40 (see FIGS. 4–5). In this embodiment, the fibrous material can also have accumulations or beads of silicon or other similar materials positioned around outer peripheries and/or around the opening 63 thereof. In a second or alternative embodiment, the first or primary valve 62' is preferably formed of a Neoprene material as understood by those skilled in the art, e.g., Nylon and/or Lycra material, such as used in dive suits or other type of applications (see FIGS.

11–13). The Neoprene material preferably has a closed-cell configuration and is laser cut for forming the valve. The first valve 62, 62' preferably has a stretching or elastic range to readily accommodate, e.g., auto-reduction, trocars or other instruments having a diameter of about 4 millimeters to about 13 millimeters as understood by those skilled in the art while still maintaining pneumoperitoneum. The second valve 66 preferably has this range as well, but individually can even have a greater range, e.g., 0 mm to 13 or 14 mm. Accordingly, with the first and second valve 62, 66 in combination, the trocar system advantageously can receive different diameter instruments without the necessity of switching cannulas or valve systems. Notably, the first valve 62, 62' is also preferably fixedly secured to the end housing, e.g., preferably by the outer peripheries thereof between lips, edges, or inwardly extending projections of portions of the housing 60, to enhance guiding, sealing, and other performance criteria of the primary valve 62 in the trocar system.

The second valve 66 preferably has an annular flange portion 71 for enhancing positioning of the second valve 66 within the end housing 60, annular-shaped sidewalls 68 connected to the annular flange and extending distally when positioned in the end housing, and at least a pair of valve flaps 69 connected to and extending inwardly from the sidewalls 68 and/or flange portion 71. The sidewalls, for example, can extend distally of the end housing so that the flange portion 71 retains only portions of the valve within the end housing and yet slidably or in a spaced-apart relation have other portions which are positioned within the proximal portion of the cannula body. The pair of valve flaps 69 have at least one slit along common peripheral edges thereof through which the trocar body 41 extends. The second valve 66 also preferably has ribs or rib members connected to, e.g., formed integrally therewith as a single piece, the sidewalls 68 as illustrated to reduce drag as will be understood by those skilled in the art. The second valve is also preferably impregnated with a lubricant such as an oil material to enhance performance of the valve.

The end housing 60 has a substantially annular shape, has a first opening 58 at a proximal end, and has a second opening 59 at a distal end. The first valve 62 is positioned adjacent the first opening 58, and the second valve is positioned spaced-apart from the first valve 62 and adjacent the second opening 59. The outer surface of the end housing 60 is roughened to enhance gripping and rotating thereof by a hand of a user when readily detaching the end housing 60 from the proximal portion of the cannula body 31. The proximal end portion of the cannula body 31 has at least one end housing mating portion 26 associated therewith and the end housing 60 also has at least one cannula body mating portion 27 associated therewith so that the end housing 60 matingly attaches to the cannula body 31 in a secured position and whereby movement of the end housing 60, e.g., rotational, by a hand of a user releases, e.g., unsecures or unlocks, the respective mating portions 26, 27 for ready removal of the end housing 60 by the user with the first and second valves 62, 66 positioned therein and so that specimens, e.g., tissue, can be readily removed from the cannula body 31 without damage by the first and second valves 62, 66. The cannula body 31 is preferably formed of a clear plastic material so that direct visualization of specimen removal and instrument passage can be advantageously provided. This, for example, allows various types of cutting, gripping, or other types of tools to be inserted through the cannula 30 for various endoscopic procedures.

According to yet another aspect of the present invention, the trocar 40, or spike or obturator if used as well, of the trocar system 20 preferably has an elongate trocar body 41 for extending through the cannula 30. The elongate trocar body 41 has a sharpened distal end portion 42, a medial portion 43 thereof including a first section 43' having a first diameter and a second section 43" having a second diameter, and a proximal portion 44 having a third diameter. The second diameter is preferably smaller than the first diameter. The third diameter is preferably larger or greater than the first diameter. The trocar 40 also has a handle 50 connected to a proximal end portion 44 of the trocar body 41 for gripping of and handling of the trocar 40 by a hand H of a user U and a shield 45 slidably mounted to the medial portion 43 of the trocar body 41 and biased in an extended position so that a distal end 42' of the shield 45 coveringly protects the sharpened distal end 42 of the trocar body 41 until pressure is applied thereagainst so that the shield 45 slidably moves toward the proximal portion 44 of the trocar body 41 in a retracted position. The shield 45 preferably has a fourth diameter which is at least equal to or less than the third diameter as illustrated.

The shield 45 has a tubular-shaped shield body 47 that substantially surrounds the medial portion 43 of the trocar body 41 and biasing means, e.g., provided by a spring 48 or other biasing member, positioned between the outer surface of the second section 43" of the medial portion 43 of the trocar body 41 and an inner surface of the tubular-shaped shield body 47, and positioned in contact with and extending between the first section 43' and an inwardly extending shoulder 51 of shield 45 that extends inwardly. The trocar body 41 preferably includes a trocar body transition region having an outer surface extending outwardly from the medial portion 43 to the proximal portion 44, forming a shield stop 49 when the shield 45 is biased to the retracted position. The shield stop 49 is preferably a first shield stop, and a second shield stop 46, such as provided by a rod or pin member can also or alternatively be connected to the trocar body 41 and cooperates with the shield body 47, e.g., to extend through a slot formed therein, to provide an alternative or an auxiliary stop for the shield body 47 when moving to the retracted position.

The sharpened distal end portion 42, e.g., preferably having a pyramidal tip, of the trocar 40 preferably has a fifth diameter. The fifth diameter is preferably larger than the second diameter of the medial portion 43" of the trocar body 41. The shield body 47 also preferably has a beveled distal end which corresponds to the shape and position of the sharpended distal end portion 42 and which extends beyond a distal end of the sharpened distal end portion 42 of the trocar body 41. This shield body can, for example, have a protruding section as illustrated or have other shaped protruding section, e.g., a nosed or other tip with which contact allows the shield body 47 to retract and yet not significantly damage the object, tissue or other item to which it abuttingly contacts.

As illustrated in FIGS. 1–13, the present invention also includes a method of handling a trocar system 20. The method includes gripping a cannula 30 with fingers F of a hand H of a user U so that the fingers F abuttingly contact at least one support web 38, 39 connected to and extending outwardly from a body 31 of the cannula 30 and slidably positioning a trocar 40 through the cannula body 31 when being gripped by the fingers F of the hand H of the user U.

The present invention also includes a method of using a trocar system 20 having the steps of detaching a cannula end housing 60 from a proximal end portion of a cannula body and removing tissue or other specimen as understood by those skilled in the art from the cannula body 31. The method can also include the end housing 60 having at least one valve 62, 66 positioned therein. The cannula end housing 60 and the cannula body 31 each have a substantially annular shape, and the cannula body 31 has a medial portion 33 having a first diameter and a proximal portion 34 connected to the medial portion 33 and having a second diameter. The second diameter is preferably larger or greater than the first diameter. The method can further include the detaching step including rotating the cannula end housing 60 a preselected rotational direction, e.g., counter-clockwise, and the at least one valve including a first and a second valve 62, 66 each connected to the cannula end housing 60 (see FIGS. 3–5 and 9–13).

Additionally, the present invention can include a method of using a trocar 40. The method preferably has the steps of inserting a trocar 40 through the body 31 of a cannula 30, retracting a shield 45 of the trocar 40 from a distal end portion 42 of the trocar 40 toward a proximal end portion 44 of the trocar 40 responsive to pressure on a distal end portion 42' of the shield 45, and stopping the retracting of the shield 45 by the use of a transition region 49 between a medial portion 43' of the trocar 40 and a proximal portion 44 of the trocar body 41 or by the use of another stop member. The method can also include the trocar 40 having a handle 50 connected to a proximal portion 44 thereof, the handle 50 has a thumb rest 53 positioned on an outer surface thereof, and the step of inserting preferably includes pressing the thumb of a user on the thumb rest 53 of the handle 50 when passing through the cannula body 31.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

The invention claimed is:

1. A trocar system comprising:
    a cannula having an elongate cannula body, the cannula body including medial and distal portions thereof having a first diameter and a proximal portion thereof connected to the medial portion and having a second diameter, the second diameter being larger than the first diameter; and
    a trocar having an elongate trocar body for extending through the cannula, the elongate trocar body having a sharpened distal end portion, a medial portion thereof including a first section having a first diameter and a second section having a second diameter smaller than the first diameter, a proximal portion having a third diameter, the third diameter being larger than the first diameter, a handle connected to a proximal end portion of the trocar body for gripping of and handling of the trocar by a hand of a user, and a shield slidably mounted to the medial portion of the trocar body and having a tubular-shaped shield body that substantially surrounds the second section of the medial portion of the trocar body and having a fourth diameter being equal to or less than the third diameter and biased by biasing means in an extended position so that a distal end of the shield coveringly protects the sharpened distal end of the trocar body until pressure is applied thereagainst so that the shield slidably moves toward the proximal portion of the trocar body in a retracted position, and a shoulder extending radially inwardly from a second portion of the inner surface of the shield body to define a shield stop positioned to provide a stop for the shield body when in an extended position, the biasing means positioned substantially between an outer surface of the second section of the medial portion of the trocar body and a first portion of an inner surface of the tubular-shaped shield body and extending between and in contact with a distal portion of the first section of the medial portion of the trocar body and a proximal portion of the shield stop.

2. A trocar system as defied in claim 1, wherein the shield stop is a first shield stop, wherein the trocar body further includes a trocar body transition region located between the medial portion of the trocar body and the proximal portion of the trocar body, the transition region having an outer surface extending outwardly from the medial portion to the proximal portion and defining a second shield stop when the shield is biased to the retracted position, and wherein the shield body is biased by the biasing means so that when pressure is applied to the shield body, the shield body slidably moves toward the proximal portion of the trocar body and contacts the second shield stop when in a fully retracted position.

3. A trocar system as defined in claim 1, wherein the sharpened distal end portion includes a pyramidal tip and a base having a fifth diameter, the fifth diameter being larger than the fourth diameter of the medial portion of the trocar body.

4. A trocar system as defined in claim 1, wherein the shield body has a distal end which extends beyond a distal end of the sharpened distal end portion of the trocar body, wherein the shield stop is a first shield stop, and wherein a second shield stop is connected to the trocar body and cooperates with the shield body to provide an auxiliary stop for the shield body when moving to the retracted position.

5. A trocar comprising:
    an elongate trocar body for extending through a cannula, the elongate trocar body having a sharpened distal end portion, a medial portion thereof having a first diameter, and a proximal portion having a second diameter, the second diameter being larger than the first diameter, the medial portion includes a first section having the first diameter and a second section having a fourth diameter smaller than the first diameter;
    a handle connected to a proximal end portion of the trocar body for gripping of and handling of the trocar by a hand of a user;
    a shield slidably mounted to the medial portion of the trocar body and biased by a biasing means in an extended position so that a distal end of the shield coveringly protects the sharpened distal end of the trocar body until pressure is applied thereagainst so that the shield slidably moves toward the proximal portion of the trocar body in a retracted position, the shield having a third diameter equal to or less than the second diameter, the shield has a tubular-shaped shield body that substantially surrounds the second section of the medial portion of the trocar body, the biasing means is positioned substantially between an outer surface of the second section of the medial portion of the trocar body and an inner surface of the tubular-shaped shield body; and
    a shoulder extending radially inwardly from the inner surface of the shield body to define a shield stop positioned to provide a stop for the shield body when in an extended position, and the biasing means extends between and is in contact with a distal portion of the first section of the medial portion of the trocar body and a proximal portion of the shield stop.

6. A trocar as defined in claim 5, wherein the shield stop is a first shield stop, wherein the trocar body further includes a trocar body transition region located between the medial portion of the trocar body and the proximal portion of the trocar body, the transition region having an outer surface extending outwardly from the medial portion to the proximal portion and defining a second shield stop when the shield is biased to the retracted positioned, and wherein the shield is biased by the biasing means so that when pressure is applied to the shield body, the shield body slidably moves toward the proximal portion of the trocar body and contacts the second shield stop when in a fully retracted position.

7. A trocar as defined in claim 5, wherein the handle includes a distal handle portion having a fourth diameter and a proximal handle portion having a fifth diameter, the distal handle portion connected to the proximal portion of the trocar body to provide handling of the trocar by a hand of a user, the fifth diameter of the proximal handle larger than the fourth diameter to provide gripping of the handle by the user.

8. A trocar comprising:
an elongate trocar body having:
a sharpened distal end portion adapted to extend through a cannula,
a medial portion including a first section having a first diameter and a second section having a second diameter smaller than the first diameter,
a proximal portion having a proximal first end portion, a proximal second end portion having a third diameter larger than the first diameter, and an elongate body portion extending between the proximal first end portion and the proximal second end portion, and
a transition region located between the first section of the medial portion having the first diameter and the proximal portion having the third larger diameter to define a first shield stop positioned to provide a stop for the shield body when in a fully retracted position;
a shield having a proximal shield end, a distal shield end, and a shield body extending therebetween slidably mounted to the medial portion of the trocar body and biased by biasing means in an extended position so that the distal shield end coveringly protects the sharpened distal end portion until pressure is applied thereagainst so that when pressure is applied to the shield body the shield slidably moves toward the proximal portion of the trocar body and contacts the shield stop when in the fully retracted position, a shoulder extending radially inwardly from an inner surface of the shield body to define a second shield stop positioned to provide a stop for the shield body when in an extended position, the shield body substantially surrounding the second section of the medial portion of the trocar body, the biasing means positioned substantially between an outer surface of the second section of the medial portion of the trocar body and an inner surface of the shield body and extending between and in contact with a distal end of the first section of the medial portion and the second shield stop.

9. A trocar as defined in claim 8, wherein a pin member is connected to the trocar body and cooperates with the shield body to thereby provide an auxiliary stop for the shield body when moving to the retracted position.

10. A trocar as defined in claim 8, further comprising a handle including a distal handle portion having a fourth diameter and a proximal handle portion having a fifth diameter, the distal handle portion connected to the proximal first end portion of the proximal portion of the trocar body to provide handling of the trocar by a hand of a user, the fifth diameter of the proximal handle larger than the fourth diameter to provide gripping of the handle by the user.

* * * * *